United States Patent

Cölln et al.

[11] 4,154,780
[45] May 15, 1979

[54] PREPARATION OF DITHIOPHOSPHORIC ACID DIESTER-HALIDES

[75] Inventors: Reimer Cölln; Hermann Arold, both of Wuppertal, Fed. Rep. of Germany; Vidyanatha A. Prasad, Kansas City, Mo.

[73] Assignees: Bayer Aktiengesellschaft, Leverkusen, Fed. Rep. of Germany; Mobay Chemical Corporation, Pittsburgh, Pa.

[21] Appl. No.: 783,371

[22] Filed: Mar. 31, 1977

[30] Foreign Application Priority Data

Apr. 8, 1976 [DE] Fed. Rep. of Germany ....... 2615342

[51] Int. Cl.$^2$ ................................................ C07F 9/20
[52] U.S. Cl. ..................................... 260/973; 260/960
[58] Field of Search ................................ 260/973, 960

[56] References Cited

U.S. PATENT DOCUMENTS

| 3,327,026 | 6/1967 | Shindo et al. .......................... 260/973 |
| 3,419,643 | 12/1968 | Price .................................... 260/973 |

FOREIGN PATENT DOCUMENTS 184863 10/1966 U.S.S.R. .................................... 260/960

Primary Examiner—Anton H. Sutto
Attorney, Agent, or Firm—Sprung, Felfe, Horn, Lynch & Kramer

[57] ABSTRACT

A process for the preparation of a dithiophosphoric acid diester-halide of the formula

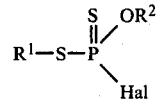

in which
R$^1$ is alkyl with 1 to 10 carbon atoms, aralkyl with 1 to 6 carbon atoms in the alkyl radical, or alkoxyalkyl or alkylthioalkyl with 1 to 5 carbon atoms in each alkyl radical,
R$^2$ is alkyl with 1 to 8 carbon atoms, and
Hal is halogen, which comprises reacting an S-alkyl or S-aralkyl ester of a dithiophosphoric acid dihalide of the formula

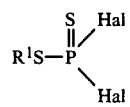

with about a 5 to 300% molar excess of an alcohol of the formula

R$^2$OH in the presence of about a 5 to 300% molar excess of a tertiary pyridine base or tertiary aralkyl-alkylamine at a temperature between about −10° and +60° C. Advantageously the tertiary base is pyridine, 2-, 3- or 4-methyl-pyridine, 4-ethyl-pyridine, 5-ethyl-2-methyl-pyridine, 2,4- or 2,6-dimethyl-pyridine, 2,4,6-trimethyl-pyridine, quinoline, isoquinoline, 2-, 4- or 6-methyl-quinoline, 6-chloro-2-methyl-quinoline, 2-chloro-4-methyl-quinoline, 8-chloro-2-methyl-quinoline or dimethylbenzylamine, the reaction is carried out at about 0° to 30° C., the alcohol is ethanol employed in about a 15 to 30% molar excess, about a 20 to 210% molar excess of the tertiary base is employed, R$^1$ is alkyl with 1 to 8 carbon atoms, aralkyl with 1 to 3 carbon atoms in the alkyl radical, or alkoxyalkyl or alkylthioalkyl with 1 to 3 carbon atoms in each alkyl radical and Hal is chlorine.

13 Claims, No Drawings

PREPARATION OF DITHIOPHOSPHORIC ACID DIESTER-HALIDES

The present invention relates to a novel process for the preparation of certain dithiophosphoric acid diester-halides which can be used as intermediates for the synthesis of various insecticidally and acaricidally active compounds according to U.S. Pat. No. 3,862,957, German Published Specification OS No. 2,327,377 and Published Japanese Patent Application No. 49-86,347.

It is known from U.S.S.R. Pat. No. 184,863 that the O,S-(dialkyl, diaryl or monoaryl-monoalkyl) diesters of dithiophosphoric acid chloride are obtained when the S-(alkyl or aryl) esters of dithiophosphoric acid dichloride are reacted with alcohols or phenols in the presence of trialkylamines in organic solvents or without acid acceptors and without solvents. However, this process has the disadvantage that the products concerned are obtained only in very poor yields and in a highly impure form including unconverted starting materials and dithiophosphoric acid triesters.

The yields are therefore only between 20 and 65% of theory. With the aid of Example 1 of the abovementioned U.S.S.R. Pat. No. 184,863, that is to say the reaction product obtained from the S-n-butyl ester of dithiophosphoric acid dichloride and a 10% strength molar excess of n-butanol in the presence of an equimolar amount of triethylamine in benzene, it was possible to show that the dithiophosphoric acid diester-chloride is obtained only in 64% yield. A further reaction of equimolar amounts of the S-n-propyl ester of dithiophosphoric acid dichloride, ethanol and triethylamine in benzene under comparable conditions shows that, contrary to the assertions in the cited publication, the desired diester monochloride is producible only in yields of about 40% of theory, as shown in the comparison experiments hereinbelow. In accurate, the yields of 87 and 69% given in the cited patent specification must relate to the technical grade products, that is to say a mixture of starting materials, the desired diester-monochloride and triesters. The usefulness of this process in practice is therefore severely restricted.

Therefore, great interest exists in a process which possesses none of these defects and gives the desired products not only in good yields but also in high purity.

The present invention now provides a process for the preparation of a dithiophosphoric acid diester-halide of the general formula

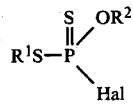   (I), in which
R$^1$ represents alkyl with 1 to 10 carbon atoms, aralkyl with 1 to 6 carbon atoms in the alkyl radical or alkoxyalkyl or alkylthioalkyl with 1 to 5 carbon atoms in each alkyl radical,
R$^2$ represents alkyl with 1 to 8 carbon atoms, and
Hal denotes halogen, preferably chlorine,
in which an S-alkyl or S-aralkyl ester of a dithiophosphoric acid dihalide, of the formula

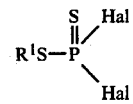   (II), in which
R$^1$ and Hal have the above-mentioned meanings,
is reacted with about a 5 to 300% molar excess of an alcohol of the general formula

R$^2$OH   (III), in which
R$^2$ has the above-mentioned meaning, using about a 5 to 300% molar excess of a tertiary pyridine base or tertiary aralkyl-alkylamine, at a temperature of between about $-10°$ and $+60°$ C., optionally in the presence of an organic solvent.

Preferably, R$^1$ represents straight-chain or branched alkyl with 1 to 8 carbon atoms (such as methyl, ethyl, n-propyl, isopropyl, n-butyl, sec.-butyl, isobutyl, tertiary butyl, n-pentyl, n-hexyl, 3-methylbutyl, 2,3-dimethylbutyl, 2,2-dimethylhexyl and 2-ethylhexyl), aralkyl with 1 to 3 carbon atoms in the alkyl radical (such as benzyl, 2-phenylethyl or 3-phenyl-n-propyl), or alkoxyalkyl or alkylthioalkyl with 1 to 3 carbon atoms in each alkyl radical (such as methoxyethyl, ethoxyethyl, n- or iso-propoxyethyl, 2-ethoxy-1-methyl-ethyl, ethylthiomethyl, ethylthioethyl, n- or iso-propylthioethyl and 2-ethylthio-1-methyl-ethyl), and R$^2$ represents straight-chain or branched alkyl with 1 to 4 carbon atoms (namely methyl, ethyl, n-propyl, isopropyl, n-butyl, sec.-butyl, isobutyl and tertiary butyl, the particularly preferred radical being ethyl).

It is extremely surprising that, under these reaction conditions, the process according to the invention can proceed in such a ready and uniform manner and can give the desired end product of the formula (I)—which hitherto could be prepared only in poor yields by the abovementioned methods—in high purity and very good yields; this is because it was not to be expected that an increase in yield of about 20-40% would be achieved by using a tertiary pyridine base or a tertiary aralkyl-alkylamine in place of a tertiary trialkylamine. Furthermore, it was not foreseen that there would be a considerable shortening of the reaction time coupled with very good yields of the desired diester-halide when an excess of an alcohol and/or tertiary base is used, because it was assumed that a greater amount of unconverted starting material would be obtained as a result of the shortened reaction time and that the excess of alcohol would effect a displacement of the reaction in favor of the undesired triester; astonishingly, this does not occur.

The process according to the invention has a number of advantages, viz. the simple manner in which it can be carried out industrially with short reaction times, the high purity and good yield.

If, for example, the S-benzyl ester of dithiophosphoric acid dichloride and ethanol are used as the starting materials and 4-methyl-pyridine is used as the substituted pyridine base, the course of the reaction according to the process can be represented by the following equation:

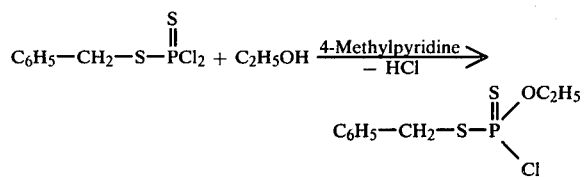

The S-alkyl and S-aralkyl esters of dithiophosphoric acid dihalides (II), which are to be used as starting materials, are already known, e.g., U.S.S.R. Pat. Nos. 175,962, 185,902 and 187,912.

Examples which may be mentioned individually are: the S-methyl, S-ethyl, S-n-propyl, S-iso-propyl, S-n-butyl, S-iso-butyl, S-sec.-butyl, S-tertiary butyl, S-n-pentyl, S-n-hexyl, S-(3-methylbutyl), S-(2,3-dimethylbutyl), S-(2,2-dimethylhexyl), S-(2-ethylhexyl), S-benzyl, S-(2-phenylethyl), S-(3-phenylpropyl), S-(methoxyethyl), S-(ethoxyethyl), S-(n- and iso-propoxyethyl), S-(2-ethoxy-1-methyl-ethyl), S-(ethylthiomethyl), S-(ethylthioethyl), S-(n- and isopropylthioethyl) and S-(2-ethylthio-1-methylethyl) esters of dithiophosphoric acid dichloride.

The alcohols (III), which are also to be used as starting materials, are known from the literature and can also be prepared easily on an industrial scale. Examples of these alcohols which may be mentioned individually are: methanol, ethanol, propan-(1 or 2)-ol, butan-2-ol, 2-methylpropan-1-ol and 2-methyl-propan-2-ol.

The process according to the invention can be carried out with or without the additional use of suitable solvents and diluents. Solvents and diluents which can be used are virtually all inert organic solvents, especially aliphatic and aromatic, optionally chlorinated hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

As indicated above, the acid-binding agents used are tertiary pyridine bases, for example pyridine, 2-, 3- or 4-methyl-pyridine, 4-ethyl-pyridine, 5-ethyl-2-methyl-pyridine, 2,4- or 2,6-dimethyl-pyridine and 2,4,6-trimethyl-pyridine, quinoline, isoquinoline, 2-, 4- or 6-methyl-quinoline, 6-chloro-2-methyl-quinoline, 2-chloro-4-methyl-quinoline or 8-chloro-2-methyl-quinoline, and tertiary aralkyl-alkylamines, for example dimethylbenzylamine.

The reaction temperature can be varied within a fairly wide range. In general, the reaction is carried out at between −10° and +60° C., preferably at about 0° to 40° C. and especially between about 0° and +30° C.

In general, the reaction is allowed to proceed under normal pressure.

In order to carry out the process according to the invention, the alcohols and the tertiary bases are always employed inexcess, as has been indicated. Appropriately, the particular dithiophosphoric acid ester-dihalide is initially introduced, optionally in one of the abovementioned solvents, and reacted using, preferably, about a 10–100%, and in particular about 15–30%, molar excess of the alcohol and preferably about a 20–210% molar excess of the tertiary base. In order to complete the conversion, the batch is subsequently stirred for some further time (half an hour to fifteen hours) at the temperatures indicated above (preferably 0° to 40° C.). Aqueous hydrochloric acid is then added to the batch and the layers are separated. The organic phase is worked up in the customary manner by washing, drying and distilling off the solvent.

The products are usually colorless to slightly yellow colored liquids which can be identified and characterized by their refractive index or by gas chromatography.

As already mentioned, the dithiophosphoric acid diester-halides which can be prepared according to the process serve as intermediate products for syntheses of insecticidal and acaricidal active compounds.

The examples which follow illustrate the process according to the invention in more detail. In these examples, the term "net yield" denotes the yield of end product (I) which is actually present and determined by analysis, relative to the amount of (II) taken, without the foreign substances entering into the calculation of the yield.

EXAMPLES OF THE PROCESS ACCORDING TO THE INVENTION

EXAMPLE 1

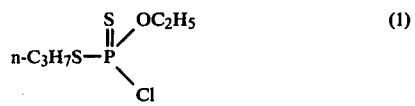

484 g (4 mol) of 2,4,6-trimethyl-pyridine were added in the course of 30 minutes to a mixture, which had been prepared at temperatures below 15° C., of 418 g (2.0 mol) of the S-n-propyl ester of dithiophosphoric acid dichloride, 600 ml of wash benzine with a boiling range of 100°–140° C. and 120 g (2.6 mol) of ethanol, at an internal temperature of 15° C., while stirring and with external cooling, and the batch was stirred for 6.5 hours at 15°–20° C. In order to work up the reaction mixture, 10% strength hydrochloric acid was added, at temperatures below 10° C., with external cooling and while stirring, until the aqueous phase had a pH value of 1. After separating off the aqueous layer, the organic phase was rinsed with 100 ml of 1% strength hydrochloric acid and the solvent was then stripped off under reduced pressure at a maximum of 60° C. According to the gas chromatogram, the slightly yellowish liquid residue (422 g) contained 96.0% of the S-n-propyl O-ethyl diester of dithiophosphoric acid chloride and 3.0% of the S-n-propyl O,O-diethyl triester of dithiophosphoric acid. The net yield was thus 92.6% of theory.

Further examples are given in Table 1 which follows and in which the essential reaction conditions are indicated:

Table 1

Examples of the reaction according to the equation

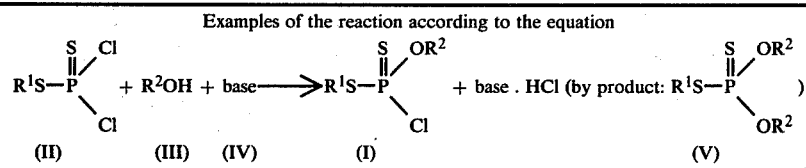

| Ex. No. | Starting materials and amounts employed in mols (II) R¹ | mol | (III) R² | mol | (IV) base | mol | Solvent | Reaction temperature (°C.) | Reaction time (hours) | Yield of crude product (g) | Content according to the gas chromatogram (I) (%) | (V) (%) | Net yield of (I) (% of theory) |
|---|---|---|---|---|---|---|---|---|---|---|---|---|---|
| 2 | n-C₃H₇— | 0.2 | C₂H₅— | 0.26 | 4-methyl-pyridine | 0.4 | 100 ml toluene | 15° | 3 | 42.9 | 95.0 | 4.0 | 93.2 |
| 3 | n-C₄H₉— | 0.1 | C₂H₅— | 0.13 | 2,4,6-tri-methyl-pyridine | 0.28 | 30 ml toluene | 15° | 3 | 22.6 | 96.6 | 2.1 | 93.8 |
| 4 | iso-C₃H₇— | 0.05 | C₂H₅— | 0.065 | 2,4,6-tri-methyl-pyridine | 0.14 | 15 ml toluene | 15° | 3 | 10.4 | 91.7 | 0.9 | 87.2 |
| 5 | n-C₈H₁₇— | 0.05 | C₂H₅— | 0.065 | 2,4,6-tri-methyl-pyridine | 0.14 | 15 ml toluene | 15° | 3 | 13.9 | 95.8 | 0.1 | 92.2 |
| 6 | C₆H₅—CH₂— | 0.025 | C₂H₅— | 0.033 | 2,4,6-trimethyl-pyridine | 0.07 | 10 ml toluene | 15° | 2 | 6.2 | 90.3 | 5.2 | 80.4 |
| 7 | C₂H₅OCH₂CH₂— | 0.05 | C₂H₅— | 0.065 | 2,4,6-trimethyl-pyridine | 0.14 | 15 ml toluene | 15° | 2 | 11.6 | 93.2 | 2.1 | 86.9 |
| 8 | n-C₃H₇— | 2.0 | C₂H₅— | 2.15 | 2,4,6-trimethyl-pyridine | 5.78 | — | 15° | 0.5 | 430 | 86.0 | 6.2 | 84.5 |
| 9 | n-C₃H₇— | 1.0 | C₂H₅— | 2.0 | N,N-dimethyl-benzyl-amine | 1.9 | 600 ml toluene | 0° to 5° | 15 | 209 | 94.5 | 3.8 | 90.3 |
| 10 | n-C₃H₇— | 0.5 | C₂H₅— | 1.0 | 2,4,6-trimethyl-pyridine | 0.95 | 300 ml toluene | 0° to 5° | 7.5 | 98.7 | 94.6 | 1.7 | 85.4 |
| 11 | n-C₃H₇— | 0.5 | C₂H₅— | 1.0 | 2,4,6-trimetyl-pyridine | 0.95 | 300 ml toluene | 20° | 3.0 | 99.6 | 92.9 | 3.5 | 84.6 |
| 12 | n-C₃H₇— | 0.1 | C₂H₅— | 0.2 | 2-methyl-5-ethyl-pyridine | 0.19 | 60 ml toluene | 0° to 5° | 15 | 19.5 | 91.4 | 2.8 | 81.5 |
| 13 | n-C₃H₇— | 0.1 | C₂H₅— | 0.2 | quinoline | 0.19 | 60 ml toluene | 20° | 15 | 19.9 | 92.3 | 3.9 | 84.0 |
| 14 | CH₃— | 0.5 | C₂H₅— | 0.65 | 2,4,6-trimethyl-pyridine | 1.0 | 300 ml ligroin | 0° to 5° | 6.5 | 87.9 | 91.6 | 4.4 | 84.5 |
| 15 | CH₃— | 0.25 | n-C₃H₇— | 0.5 | 2,4,6-trimethyl-pyridine | 0.475 | 150 ml ligroin | 0° to 5° | 15 | 47.8 | 90.5 | 4.9 | 84.5 |
| 16 | n-C₃H₇— | 0.25 | CH₃— | 0.275 | 2,4,6-trimethyl-pyridine | 0.475 | 150 ml ligroin | 0° to 5° | 5 | 42.8 | 93.6 | 3.1 | 78.3 |

EXAMPLE 17

A solution of 215.5 g. (1.0 mol) of the 97% pure S-n-propyl ester of dithiophosphoric acid dichloride in 350 ml of toluene was cooled to −10° C. and 214.0 g (2.0 mol) of 2,4-dimethyl-pyridine were added rapidly at a temperature of at most 0° C., while stirring. 55.2 g (1.2 mol) of ethanol were added dropwise to this mixture in the course of 2.5 hours, during which time a reaction temperature of −5° to 0° C. was maintained. The mixture was then stirred for a further 2.5 hours at 0° C. 750 ml of water were then added to 110 g of concentrated hydrochloric acid and this mixture was added to the reaction mixture. The latter was then stirred for a further 15 minutes at 0° C. In order to achieve a clear phase separation, a further 100 ml of toluene were added to the mixture. The organic layer was separated off and washed with 500 ml of water. The two aqueous layers were combined and extracted with 150 ml of toluene and the layers were separated and the organic phases were combined; the aqueous layer was treated with NaOH in order to recover 2,4-dimethyl-pyridine. The bulk of the toluene was then removed from the organic layer by distillation under reduced pressure. The remaining toluene was removed by steam distillation and the low-boiling impurities, such as, for example, disulphides, were also removed at the same time. The reaction product was separated off and dried in vacuo. The yield of the crude S-n-propyl O-ethyl diester of dithiophosphoric acid chloride was 202.8 g (92.8% of theory);

the product was 96.9% pure and this corresponded to a net yield of 89.9%.

EXAMPLE 18

13.6 g of 100% pure 2,4-dimethyl-pyridine were combined with 489.4 g of recovered 2,4-dimethyl-pyridine/-toluene solution (corresponding to a content of 146.9 g of 2,4-dimethyl-pyridine) and this gave a total amount of 160.5 g (1.5 mol) of 2,4-dimethyl-pyridine. 570 ml of toluene, the amount of 2,4-dimethyl-pyridine indicated above and 217.7 g (1.0 mol) of the S-n-propyl ester of dithiophosphoric acid dichloride were initially introduced. Starting at a reaction temperature of 10° C., 56.6 g (1.23 mol) of ethanol were added dropwise to the reaction mixture in the course of two and a half hours and during this addition the temperature varied between 17° and 22° C. The mixture was then stirred at this temperature for three and a half hours. 51.0 g of concentrated sulphuric acid were diluted with 225 ml of water and added to the reaction mixture, which was then stirred for 20 minutes at 5° C. The reaction vessel was rinsed out with a further 275 ml of water and 70 ml of toluene and the wash solution was combined with the reaction mixture. The aqueous and organic phases were extracted, the organic layer was washed with 275 ml of recovered water and the aqueous and organic phases were extracted again. The organic layers were then combined; the first aqueous phase was treated with NaOH in order to recover 2,4-dimethyl-pyridine, although this was optional, and the second aqueous phase was reintroduced into the cycle. The combined organic phases were subjected to a steam distillation in order to remove the bulk of the toluene and the low-boiling impurities, for example dipropyl disulphide. The reaction product was separated off from the water originating from the steam distillation, dried in vacuo and filtered through a Buchner funnel. The yield of the crude S-n-propyl O-ethyl diester of dithiophosphoric acid chloride was 208.0 g (92.4%) of a 94.1% pure product and this corresponded to a net yield of 87.0%.

EXAMPLE 19

350 ml of toluene, 210.9 g (1.0 mol) of the S-n-propyl ester of dithiophosphoric acid dichloride and 133.8 g (1.25 mol) of 2,4-dimethyl-pyridine were combined successively. Starting at a temperature of 35° C., 57.5 g (1.25 mol) of ethanol were added dropwise to this mixture in the course of one hour and during the addition a reaction temperature of 35° to 40° C. was maintained. The reaction mixture was then stirred for 2.5 hours at 35° to 40° C. 25.5 g of concentrated sulphuric acid were then mixed with 150 ml of water. This mixture was added to the reaction mixture and the latter was stirred for 20 minutes at 20° C. The reaction vessel was rinsed out with a further 175 ml of water and 50 ml of toluene and the solution was combined with the reaction mixture. The aqueous and the organic phase were extracted. The aqueous layer was then washed with 60 ml of toluene. The layers were separated and the organic phases were combined; the aqueous portion was treated with NaOH in order to recover the 2,4-dimethyl-pyridine, although this was optional. The organic phase was distilled with steam in order to remove the bulk of the toluene and low-boiling impurities such as dipropyl disulphide. Finally, the reaction product was separated off from the water originating from the steam distillation and dried in vacuo. This gave 208 g of the crude S-n-propyl O-ethyl diester of dithiophosphoric acid chloride, which corresponded to a yield of crude product of 94.6%. The product was 88.2% pure, corresponding to a net yield of 84.0%.

COMPARISON EXAMPLES

COMPARISON EXAMPLE 1

(Use of triethylamine as the base in accordance with U.S.S.R. Pat. No. 184,863).

5.1 g (0.05 mol) of triethylamine were added in the course of 15 minutes to a mixture of 11.2 g (0.05 mol) of the S-n-butyl ester of dithiophosphoric acid chloride, 60 ml of benzene and 4.1 g (0.055 mol) of n-butanol, while stirring; the batch was allowed to react further for 5 hours at 35°–40° C., the reaction mixture was then washed with twice 80 ml of water at temperatures below 10° C. and the solvent was removed under reduced pressure. This gave 12.1 g of a liquid as the residue and this corresponded to a yield of crude product of 92.8% of theory. However, according to the gas chromatogram, the residue contained only 69.9% of the O,S-di-n-butyl diester of dithiophosphoric acid chloride, so that the net yield was only 64.9% of theory. The residue also contained 4.1% of the unconverted S-n-butyl ester of dithiophosphoric acid dichloride and 21.6% of the O,O,S-tri-n-butyl triester of dithiophosphoric acid as an undesired by-product.

COMPARISON EXAMPLE 2

(Use of equimolar amounts of ethanol and triethylamine)

(a) A reaction time of 1 hour.

A mixture of 4.6 g (0.1 mol) of ethanol, 10.1 g (0.1 mol) of triethylamine and 10 ml of benzene was added to a mixture of 20.9 g (0.1 mol) of the S-n-propyl ester of dithiophosphoric acid dichloride and 150 ml of benzene, at 0° to 5° C., while stirring and with external cooling, and the mixture was stirred for a further one hour at 20°–25° C. The salt-like precipitate which had formed was then filtered off, the solvent was stripped off in vacuo and the residue was distilled under reduced pressure. This gave 17.2 g of a colorless liquid which had a refractive index $n_D^{22}$ of 1.5600 and a boiling range of 75° to 84° C. under 2 mm Hg. According to the gas chromatogram, the liquid contained 67.5% of the starting material, 23% of the S-n-propyl O-ethyl diester of dithiophosphoric acid chloride and 3% of the S-n-propyl O,O-diethyl triester of dithiophosphoric acid. The net yield of the desired diester-chloride was thus only 18.1% of theory.

(b) A reaction time of 15 hours.

With a procedure that was otherwise identical to that described under (a) but with a post-reaction time of 15 hours, 15.6 g of a crude product which, according to the gas chromatogram, contained 7.2% of the starting material, 56.8% of the S-n-propyl O-ethyl diester of dithiophosphoric acid chloride and 29.7% of the S-n-propyl O,O-diethyl triester of dithiophosphoric acid, were obtained. In this case the net yield was 40.5% of theory.

COMPARISON EXAMPLE 3

(Use of 2,4,6-trimethylpyridine in place of triethylamine as the base).

When 0.1 mole of 2,4,6-trimethylpyridine was used in place of 0.1 mol of triethylamine and in other respects the procedure was precisely as in Comparison Example 2(b), 19.7 g of a crude product were obtained which, according to the gas chromatogram, contained 7.5% of unconverted starting material, 90% of the S-n-propyl O-ethyl diester of dithiophosphoric acid chloride and 2.2% of the S-n-propyl O,O-diethyl triester of dithiophosphoric acid. The net yield was thus 81.1% of theory.

COMPARISON EXAMPLE 4

The test series which follows shows that an excess of the pyridine base and of the alcohol accelerated the conversion of the S-n-propyl ester of dithiophosphoric acid dichloride without this resulting in a significant increase in the formation of the triester, compared with corresponding experiments in which triethylamine is used as the base.

The amounts of the S-n-propyl ester of dithiophosphoric acid dichloride (II a), ethanol (III a) and 2,4,6-trimethyl-pyridine (IV a) or, in place of the latter, triethylamine, which are indicated in Table 2 which follows were mixed, in a 500 ml stirred flask, at a temperature of $-15°$ to $-10°$ C. with 100 ml of toluene and the reaction mixture was then warmed to exactly 25° C. and was stirred at this temperature until 99% of the particular starting material (II a) had been converted. The time at which the experiment was discontinued was determined by comparing the size of the spots obtained by thin-layer chromatography for the reaction solutions with those obtained for a standardized comparison solution of the starting material (II a), which standardized solution corresponded to a residual content of 1% of (II a). When carried out at 30 minute intervals, this method ensured that the determination of the reaction time was sufficiently accurate for comparison purposes. (Thin layer chromatography in the system silica gel/petroleum ether-toluene, 8:2; amount applied 2 mm$^3$.) After the 99% conversion thus defined had been reached, the particular reaction mixture was immediately cooled to $-10°$ C. and stirred with 100 g of ice-water and 10 ml of concentrated hydrochloric acid and the phases were separated. The organic phase was washed twice more with, in each case, 100 ml of ice-cold water, dried and freed from the solvent under reduced pressure. Contents of the S-n-propyl O-ethyl diester of dithiophosphoric acid chloride (I a) and the S-n-propyl O,O-diethyl triester of dithiophosphoric acid (V a) were determined in the residue by gas chromatography.

It will be appreciated that the instant specification and examples are set forth by way of illustration and not limitation, and that various modifications and changes may be made without departing from the spirit and scope of the present invention.

What is claimed is:

1. A process for the preparation of a dithiophosphoric acid diester-halide of the formula $$R^1-S-P\underset{\underset{Hal}{\diagdown}}{\overset{\overset{S}{\|}}{\diagup}}OR^2$$

in which
R$^1$ is alkyl with 1 to 10 carbon atoms, aralkyl with 1 to 6 carbon atoms in the alkyl radical, or alkoxyalkyl or alkylthioalkyl with 1 to 5 carbon atoms in each alkyl radical,
R$^2$ is alkyl with 1 to 8 carbon atoms, and
Hal is halogen,
which comprises reacting an S-alkyl or S-aralkyl ester of a dithiophosphoric acid dihalide of the formula $$R^1S-P\underset{\underset{Hal}{\diagdown}}{\overset{\overset{S}{\|}}{\diagup}}Hal$$

with about a 15 to 300% molar excess of an alcohol of the formula $$R^2OH$$

in the presence of about 20 to 300% molar excess of a tertiary pyridine base or tertiary aralkyl-alkylamine at a temperature between about $-10°$ and $+60°$ C.

2. A process according to claim 1, in which the tertiary base is pyridine, 2-, 3- or 4-methyl-pyridine, 4-ethylpyridine, 5-ethyl-2-methyl-pyridine, 2,4- or 2,6-dimethyl-pyridine, 2,4,6-trimethyl-pyridine, quinoline, isoquinoline, 2-, 4- or 6-methyl-quinoline, 6-chloro-2-methyl-quinoline, 2-chloro-4-methylquinoline, 8-chloro-2-methyl-quinoline or dimethylbenzylamine.

3. A process according to claim 1, in which the reaction is carried out at about 0° to $+40°$ C.

4. A process according to claim 3, in which the reaction is carried out at about 0° to $+30°$ C.

5. A process according to claim 1, in which about a 30 to 100% molar excess of the alcohol is employed.

Table 2

Comparison Examples of the reaction according to the equation:

$$\text{n-C}_3\text{H}_7\text{S}-P\underset{\underset{Cl}{\diagdown}}{\overset{\overset{S}{\|}}{\diagup}}Cl + C_2H_5OH + \text{base} \xrightarrow{25° C.} \text{n-C}_3\text{H}_7\text{S}-P\underset{\underset{Cl}{\diagdown}}{\overset{\overset{S}{\|}}{\diagup}}OC_2H_5 + \text{base} \cdot HCl$$

(IIa)　　　　(IIIa)　　(IVa)　　　　　　(Ia)

| Comparison Example No. | Starting materials and amounts employed in mols (IIa) | (IIIa) | (IVa)* | Reaction time to reach a "99% conversion" | Yield of crude product (g) | Content according to the gas chromatogram (Ia) (%) | **(Va) (%) | Net yield of (Ia) (% of theory) |
|---|---|---|---|---|---|---|---|---|
| 4 a | 0.1 | 0.15 | 0.15 | 420 minutes | 20.1 | 88.9 | 2.8 | 81.7 |
| 4 b | 0.1 | 0.15 | 0.2 | 270 minutes | 19.9 | 89.4 | 2.8 | 81.4 |
| 4 c | 0.1 | 0.2 | 0.2 | 180 minutes | 19.7 | 89.5 | 3.1 | 80.6 |
| 4 d | 0.1 | 0.2 | 0.15 | 330 minutes | 19.9 | 89.7 | 3.3 | 81.6 |
| 4 e | 0.1 | 0.15 | 0.15 | 450 minutes | 20.6 | 64.7 | 30.9 | 60.9 |
| 4 f | 0.1 | 0.2 | 0.2 | 210 minutes | 20.8 | 62.5 | 33.1 | 59.4 |

*Base (IVa) is 2,4,6-trimethylpyridine in 4ra,b,c,d and triethylamine in 4e,f
**By-product (Va) is S-n-propyl-O,O-diethyl-dithiophosphoric acid triester 4a,b,c,d 6. A process according to claim 5, in which about a 100% molar excess of the alcohol is employed.

7. A process according to claim 1, in which about a 100 to 210% molar excess of the tertiary base is employed.

8. A process according to claim 1, in which $R^1$ is alkyl with 1 to 8 carbon atoms, aralkyl with 1 to 3 carbon atoms in the alkyl radical, or alkoxyalkyl or alkylthioalkyl with 1 to 3 carbon atoms in each alkyl radical.

9. A process according to claim 1, in which $R^2$ is ethyl.

10. A process according to claim 1, in which Hal is chlorine.

11. A process according to claim 2, in which the reaction is carried out at about 0° to +40° C., the alcohol is ethanol employed in about a 100% molar excess, about a 100 to 210% molar excess of the tertiary base is employed, $R^1$ is alkyl with 1 to 8 carbon atoms, aralkyl with 1 to 3 carbon atoms in the alkyl radical, or alkoxyalkyl or alkylthioalkyl with 1 to 3 carbon atoms in each alkyl radical and Hal is chlorine.

12. A process according to claim 11 in which the ethanol and tertiary base are each employed in about 100% molar excess.

13. A process according to claim 1 in which the reaction between the S-alkyl or S-aralkyl ester and the dithiopnosphoric acid dihalide and the aclohol is effected in the presence of a tertiary aralkyl-alkylamine.

* * * * *